US006897328B2

(12) United States Patent
Gutsche et al.

(10) Patent No.: US 6,897,328 B2
(45) Date of Patent: May 24, 2005

(54) PROCESS FOR DEACIDIFYING NATURAL FATS AND OILS

(75) Inventors: Bernhard Gutsche, Hilden (DE); Albrecht Weiss, Langenfeld (DE); Ralf Otto, Bad Fredrichshall (DE); Tycho Michel, Langenfeld (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/301,333

(22) Filed: Nov. 21, 2002

(65) Prior Publication Data

US 2003/0124694 A1 Jul. 3, 2003

(30) Foreign Application Priority Data

Nov. 21, 2001 (DE) ........................................ 101 57 067

(51) Int. Cl.$^7$ ................................................ C07C 51/43

(52) U.S. Cl. ....................... 554/206; 435/134; 435/178; 435/180; 435/198

(58) Field of Search .......................... 554/206; 435/134, 435/178, 180, 198

(56) References Cited

U.S. PATENT DOCUMENTS

| | | | | |
|---|---|---|---|---|
| 4,698,186 A | | 10/1987 | Jeromin et al. | |
| 6,398,707 B1 | * | 6/2002 | Wu et al. | 554/169 |

FOREIGN PATENT DOCUMENTS

| | | | | |
|---|---|---|---|---|
| DE | 196 00 025 | | 7/1997 | |
| DE | 199 56 599 | | 6/2001 | |
| EP | 0 192 035 | | 8/1986 | |
| WO | WO 91/14784 | | 10/1991 | |
| WO | WO 9114784 A1 | * | 10/1991 | C11C/3/10 |

* cited by examiner

*Primary Examiner*—Deborah Carr
(74) *Attorney, Agent, or Firm*—Aaron R. Ettelman; Steven J. Trzaska; Daniel S. Ortiz

(57) ABSTRACT

A single stage process for deacidifying glycerides involving:

(a) providing a glyceride having an acid value of from about 5 to 20;

(b) providing a lower alcohol;

(c) providing an enzyme catalyst immobilized on a support material; and passing a mixture of (a) and (b), over (c), thereby deacidifying the glycerides.

15 Claims, No Drawings

PROCESS FOR DEACIDIFYING NATURAL FATS AND OILS

BACKGROUND OF THE INVENTION

This invention relates generally to oleochemical raw materials and, more particularly, to a biotechnological process for deacidifying fats and oils.

PRIOR ART

Natural fats and oils always contain a proportion of free fatty acids—known in the literature as the FFA (free fatty acid) value or acid value—as a result of enzymatic decomposition processes which begin immediately after harvesting of the oil-bearing fruit. The FFA value is one of the quality criteria for fats and oils because low acid values stand for comparatively pure products rather than old, rancid products. So far as the further processing of the fats and oils is concerned, the fatty acids present are undesirable because they form soaps with the basic catalysts used, for example, in the transesterification reaction. These soaps do not react any further and have to be subsequently disposed of as waste materials. In practice, this problem is overcome by so-called "deacidification" which is a preliminary esterification step preferably carried out with methanol. In this way, the acid value is brought virtually to zero while the resulting methyl esters react off similarly to the glycerol ester in the further processing of the fats and oils and, accordingly, are not problematical.

This preliminary esterification step is normally carried out with heterogeneous catalysts, for example zinc or tin compounds, as described in DE 19956599 A1, DE 19600025 C2 and EP 0192035 B1. As explained above, the process is entirely effective so far as the desired reduction of the acid value is concerned, but is attended by the disadvantage that the catalysts have to be expensively removed, generally cannot be regenerated and hence represent a considerable burden on the process from the economic perspective. In addition, continuous operation is not possible and it has often been found that the methyl esters are split back, i.e. the reduction in the acid value is not permanent.

Accordingly, the problem addressed by the present invention was to provide an improved continuous process for the permanent deacidification of fats and oils which would be distinguished by the fact that the acid value would be permanently reduced to a value below 1, high throughputs would be achieved and the catalyst costs would be lastingly reduced in relation to the prior art through re-use.

DESCRIPTION OF THE INVENTION

The present invention relates to a process for the deacidification of natural fats and oils in which glycerides with acid values of 5 to 20 are treated with lower alcohols and free fatty acids are thus converted into esters, characterized in that the reaction is carried out in the presence of enzymes immobilized on supports with a diameter of 1 to 5 mm.

It has surprisingly been found that not only are enzymes immobilized on supports with particular diameters eminently suitable for the pre-esterification of acidic fats and oils, they also—and above all—allow high flow rates and hence high throughputs in continuous operation. The reaction products obtained preferably have acid values below 1.

Natural Fats and Oils

Basically, the process according to the invention may be applied to any natural fats and oils which, as a result of partial enzymatic decomposition, have a content of free fatty acids, i.e. have an acid value. To this extent the choice of the triglyceride is not critical. However, the process is particularly suitable for fats and oils of comparatively high quality, i.e. fats and oils with a low acid value, for example of at most 20 and preferably in the range from 10 to 15. Although, in principle, starting materials with higher acid values can be deacidified in this way, it may be that, ultimately, acid values of only 5 to 10 are reached or that high enzyme concentrations and/or long reaction times are necessary for further reductions. However, preferred raw materials are coconut oil, palm oil, palm kernel oil, sunflower oil and rapeseed oil and mixtures thereof which have acid values of 5 to 20 and preferably in the range from 10 to 15.

Alcohols

The principle of reduction of the acid value consists in esterification of the free fatty acids with alcohols, preferably lower alcohols, corresponding to formula (I):

$$ROH \quad (I)$$

in which R is a linear or branched alkyl group containing 1 to 4 carbon atoms. Typical examples are ethanol and the isomeric propanols and butanols, methanol of course preferably being used. The alcohols are normally used in quantities of 1 to 10 and preferably 2 to 5% by weight, based on the quantity of triglycerides.

Enzymes and Supports

Preferred enzymes for the process according to the invention are lipases. Typical examples of suitable lipases are the commercial products Novozym 388 L, Novozym SP 525 L, Lipozym TL 100 and Amano G. The enzymes are generally used in the form of dilute suspensions or water-based concentrates, the concentration used generally being 0.5 to 10% by weight and preferably 1 to 2% by weight, based on the quantity of triglycerides. In order to achieve continuous operation and high throughputs, the enzymes have to be immobilized on suitable supports. The determining factor in the choice of the support is not so much its chemical nature as its diameter. This must be small enough to guarantee a large surface, but on the other hand also coarse enough to guarantee a reaction at high flow rates of the starting materials. The support preferably consists of polyolefin granules and more particularly polypropylene granules with a mean diameter of 1 to 5 and preferably around 3 mm. The enzymes and supports are preferably used in a ratio by weight of 1:1 to 1:100 and more particularly 1:5 to 1:10.

Deacidification

The deacidification of the fats and oils can be carried out by methods known per se for the continuous enzymatic esterification of fatty acids. The reaction temperature is of course determined by the activity optimum of the enzymes used and is therefore in the range from 20 to 50 and preferably 25 to 35° C. The immobilized enzymes are introduced as a packing into a tube reactor and the starting material to be deacidified is passed upwards through the tube reactor, the residence time in continuous operation generally being 1 to 20 and preferably 5 to 8 h. The process may be carried out in a single stage although, in the interests of reducing the quantity of methanol to be used, it has proved to be of advantage to connect two to five reactors in series and to carry out the reaction in several stages.

EXAMPLES

Example 1

6 g of the enzyme catalyst consisting of a 1:1 mixture of SP 525 l and polypropylene granules were introduced into a glass tube. From a mechanically stirred storage vessel, a mixture of 250 g of degummed coconut oil and 5% by weight of methanol was continuously pumped through the packing at 30° by a peristaltic pump (upward stream) and the reduction in the acid value was monitored by taking samples. The results are set out in Table 1.

TABLE 1

| | Reduction of the acid value | | | | |
|---|---|---|---|---|---|
| Time [h] | 0 | 2 | 4 | 6 | 8 |
| Acid value | 8.3 | 3.9 | 2.5 | 1.7 | 0.9 |

Example 2.

The biocatalyst was filtered off and re-used another three times as described above. 1 kg of coconut oil was pre-esterified in each of the three runs. The reduction in the acid value as a function of time in the third run is shown in Table 2. It can be seen that, in principle, the activity of the catalyst remains constantly high.

TABLE 2

| | Reduction of the acid value | | | | |
|---|---|---|---|---|---|
| Time [h] | 0 | 2 | 4 | 6 | 8 |
| Acid value | 8.3 | 5.7 | 4.0 | 2.7 | 0.9 |

What is claimed is:

1. A single stage process for deacidifying glycerides comprising:

(a) providing a glyceride having an acid value of from about 5 to 20;

(b) providing a lower alcohol;

(c) providing an enzyme catalyst immobilized on a support material, wherein the support material has a mean diameter of from about 1 to 5 mm; and (d) passing a mixture of (a) and (b), over (c), thereby deacidifying the glycerides.

2. The process of claim 1 wherein the glyceride is selected from the group consisting of coconut oil, palm oil, palm kernel oil, sunflower oil, rapeseed oil, and mixtures thereof.

3. The process of claim 1 wherein the glyceride has an acid value of from about 10 to 15.

4. The process of claim 1 wherein the lower alcohol is a $C_{1-4}$ alcohol.

5. The process of claim 1 wherein the lower alcohol is methanol.

6. The process of claim 1 wherein the lower alcohol is employed in an amount of from about 1 to 10% by weight, based on the weight of the glycerides.

7. The process of claim 1 wherein the lower alcohol is employed in an amount of from about 2 to 5% by weight, based on the weight of the glycerides.

8. The process of claim 1 wherein the enzyme is a lipase.

9. The process of claim 1 wherein the enzyme is employed in an amount of from about 0.5 to 10% by weight, based on the weight of the glycerides.

10. The process of claim 1 wherein the enzyme Is employed in an amount of from about 1 to 2% by weight, based on the weight of the glycerides.

11. The process of claim 1 wherein the support material has a mean diameter of about 3 mm.

12. The process of claim 1 wherein the support material comprises polyolefin granules.

13. The process of claim 1 wherein the enzyme catalyst and support material are employed in a ratio by weight of from about 1:1 to 1:100.

14. The process of claim 1 wherein the enzyme catalyst and support material are employed in a ratio by weight of from about 1:5 to 1:10.

15. The process of claim 1 wherein the glycerides are deacidified in multiple stages, each of which employ steps (a)–(d).

* * * * *